US009055394B2

(12) United States Patent
Yanagidate

(10) Patent No.: US 9,055,394 B2
(45) Date of Patent: Jun. 9, 2015

(54) WIRELESS COMMUNICATION DEVICE AND WIRELESS COMMUNICATION SYSTEM

(71) Applicant: Olympus Corporation, Tokyo (JP)

(72) Inventor: Masaharu Yanagidate, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 140 days.

(21) Appl. No.: 13/888,703

(22) Filed: May 7, 2013

(65) Prior Publication Data

US 2013/0244580 A1    Sep. 19, 2013

Related U.S. Application Data

(63) Continuation of application No. PCT/JP2011/067434, filed on Jul. 29, 2011.

(30) Foreign Application Priority Data

Nov. 10, 2010 (JP) ................. 2010-251969

(51) Int. Cl.
   *H04B 1/00*    (2006.01)
   *H04W 4/00*    (2009.01)
   (Continued)

(52) U.S. Cl.
   CPC ........... *H04W 4/008* (2013.01); *A61B 1/00016* (2013.01); *G08C 17/02* (2013.01); *A61B 2017/00221* (2013.01); *A61B 2017/00225* (2013.01); *A61B 17/320068* (2013.01)

(58) Field of Classification Search
   CPC .... H04W 16/14; H04W 72/08; H04W 72/082
   USPC .................. 455/63.1, 67.11, 67.13
   See application file for complete search history.

(56) References Cited

U.S. PATENT DOCUMENTS

2008/0297656 A1    12/2008  Saito
2010/0071018 A1    3/2010   Kabuto

FOREIGN PATENT DOCUMENTS

EP    0 939 523 A2    9/1999
JP    07-147697 A    6/1995

(Continued)

OTHER PUBLICATIONS

International Search Report for PCT/JP2011/067434, mailing date of Oct. 25, 2011.

(Continued)

*Primary Examiner* — Lee Nguyen
(74) *Attorney, Agent, or Firm* — Westerman, Hattori, Daniels & Adrian, LLP

(57) ABSTRACT

The present invention provides a wireless communication device comprising: a wireless communication unit configured to perform wireless communication using radio waves belonging to a predetermined radio wave band between a first external device and a second external device; a proximity communication unit configured to perform proximity communication with a control terminal; and a control unit configured to cause control data, which indicates an instruction for the first external device, received from the control terminal via the proximity communication unit to be transmitted to the first external device via the wireless communication unit, the control unit adjusting a transmission timing of the control data or the data when causing the control data to be transmitted to the first external device while the first external device or the wireless communication unit sequentially transmits data to the second external device.

9 Claims, 14 Drawing Sheets

(51) Int. Cl.
  *A61B 1/00* (2006.01)
  *G08C 17/02* (2006.01)
  *H04B 7/00* (2006.01)
  *A61B 17/00* (2006.01)
  *A61B 17/32* (2006.01)

(56) References Cited

FOREIGN PATENT DOCUMENTS

| JP | 2002-232978 A | 8/2002 |
| JP | 2003-245286 A | 9/2003 |
| JP | 2008-519501 A | 6/2008 |
| JP | 2008-301249 A | 12/2008 |
| JP | 2008-306746 A | 12/2008 |
| JP | 2010-074204 A | 4/2010 |
| JP | 2010-213154 A | 9/2010 |
| WO | 2006/050410 A1 | 5/2006 |

OTHER PUBLICATIONS

Office Action dated Jul. 22, 2014, issued in corresponding Japanese Patent Application No. 2010-251969, with English Translation (4 pages).

Extended European Search Report (EESR) dated Dec. 10, 2013, issued in corresponding European Application No. 11840054.8.

FIG. 6

| CONFIGURATION OF CART 10 | DEVICE ID | OPERATION STATE | NOISE |
|---|---|---|---|
| SYSTEM CONTROLLER | CT-001 | IN OPERATION | ABSENT |
| WIRELESS COMMUNICATION DEVICE | RF-001 | IN IMAGE TRANSMISSION | ABSENT |
| MONITOR | MO-001 | IN IMAGE DISPLAY | ABSENT |
| ENDOSCOPE | ES-001 | IN OPERATION | ABSENT |
| PNEUMOPERITONEUM DEVICE | CS-001 | IN OPERATION | ABSENT |
| ULTRASONIC TREATMENT DEVICE | SS-001 | STOPPED | ABSENT |
| ELECTRIC SCALPEL | SG-001 | IN OPERATION | PRESENT |
| FOOT SWITCH | SW-001 | ELECTRIC SCALPEL CONTROL | ABSENT |
| RELAY DEVICE | BC-001 | NOT IN REMOTE CONTROLLER CONNECTION | ABSENT |

| CONFIGURATION OF CART 18 | DEVICE ID | OPERATION STATE | NOISE |
|---|---|---|---|
| SYSTEM CONTROLLER | CT-002 | IN OPERATION | ABSENT |
| WIRELESS COMMUNICATION DEVICE | RF-002 | IN IMAGE TRANSMISSION | ABSENT |
| MONITOR | MO-002 | IN IMAGE DISPLAY | ABSENT |
| ENDOSCOPE | ES-002 | IN OPERATION | ABSENT |
| SHAVER | SH-001 | STOPPED | PRESENT |
| PUMP | PU-001 | STOPPED | ABSENT |
| RELAY DEVICE | BC-002 | IN REMOTE CONTROLLER CONNECTION | ABSENT |

FIG. 7

| TRANSMISSION DESTINATION | CONTROL PARTNER | DEVICE ID | CONTROL CONTENT | RECEPTION TIME |
|---|---|---|---|---|
| RELAY DEVICE 10 | FOOT SWITCH | SW-001 | ULTRASONIC CONTROL | 10:30:25 |
| RELAY DEVICE 10 | PNEUMOPERITONEUM DEVICE | CS-001 | FLOW RATE CHANGE | 10:30:28 |

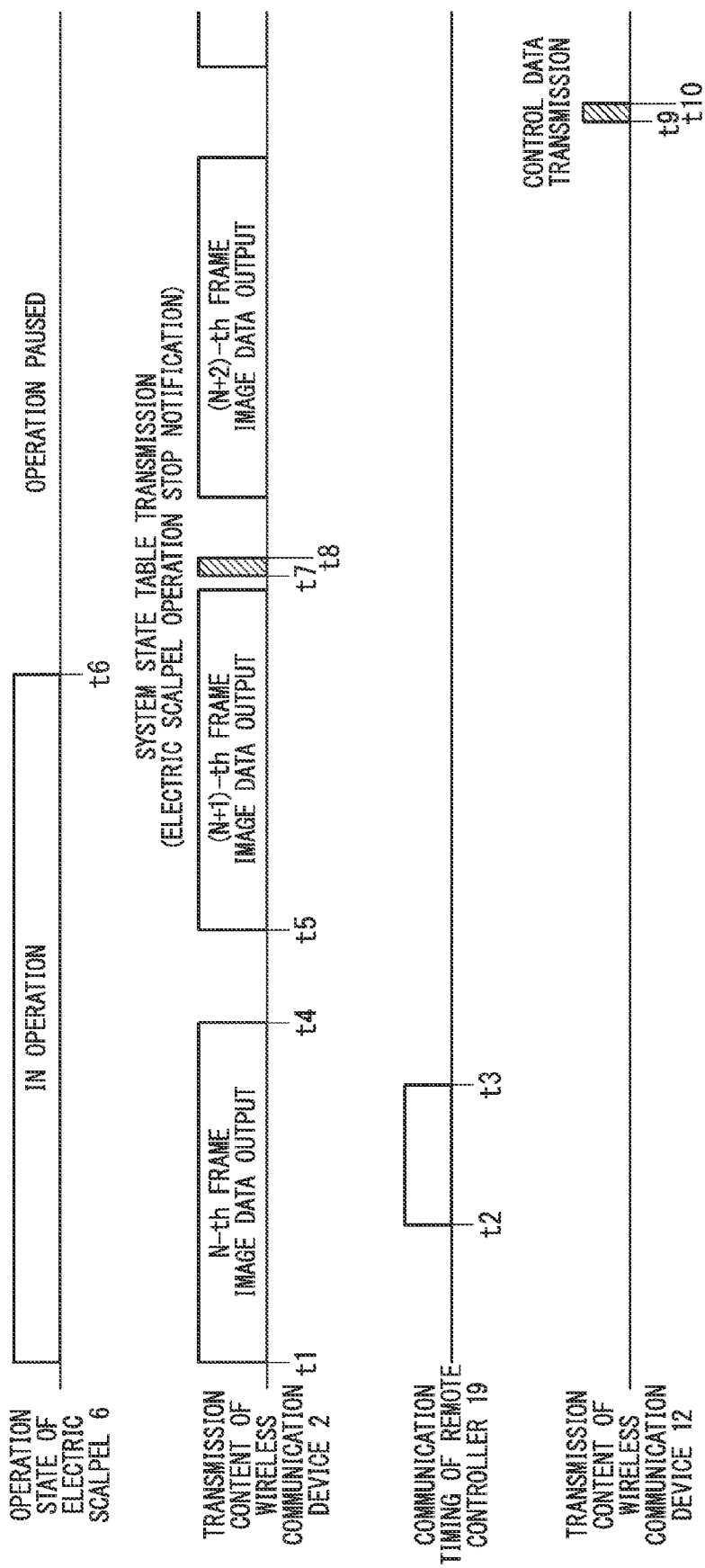

FIG. 15

| CONFIGURATION OF CART 10 | DEVICE ID | OPERATION STATE | NOISE | PRIORITY |
|---|---|---|---|---|
| SYSTEM CONTROLLER | CT-001 | IN OPERATION | ABSENT | 1 |
| WIRELESS COMMUNICATION DEVICE | RF-001 | IN IMAGE TRANSMISSION | PRESENT | 7 |
| MONITOR | MO-001 | IN IMAGE DISPLAY | ABSENT | 8 |
| ENDOSCOPE | ES-001 | IN OPERATION | ABSENT | 5 |
| PNEUMOPERITONEUM DEVICE | CS-001 | IN OPERATION | ABSENT | 4 |
| ULTRASONIC TREATMENT DEVICE | SS-001 | STOPPED | ABSENT | 3 |
| ELECTRIC SCALPEL | SG-001 | STOPPED | PRESENT | 2 |
| FOOT SWITCH | SW-001 | ELECTRIC SCALPEL CONTROL | ABSENT | 6 |
| RELAY DEVICE | BC-003 | IN REMOTE CONTROLLER CONNECTION | ABSENT | — |

| CONFIGURATION OF CART 18 | DEVICE ID | OPERATION STATE | NOISE | PRIORITY |
|---|---|---|---|---|
| SYSTEM CONTROLLER | CT-002 | IN OPERATION | ABSENT | 1 |
| SHAVER | SH-001 | STOPPED | PRESENT | 2 |
| PUMP | PU-001 | STOPPED | ABSENT | 3 |
| RELAY DEVICE | BC-004 | NOT IN REMOTE CONTROLLER CONNECTION | ABSENT | — |

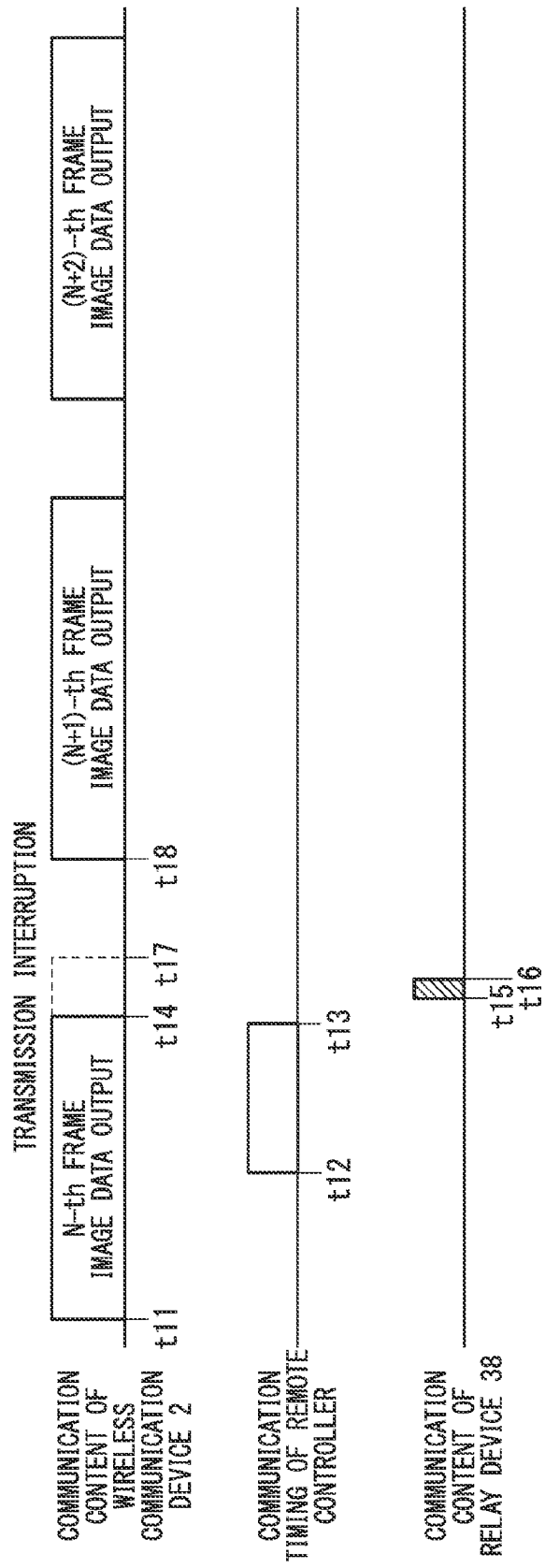

WIRELESS COMMUNICATION DEVICE AND WIRELESS COMMUNICATION SYSTEM

CROSS REFERENCE TO RELATED APPLICATIONS

This application is a continuation application based on a PCT Patent Application No. PCT/JP2011/067434, filed Jul. 29, 2011, whose priority is claimed on Japanese Patent Application No. 2010-251969, filed on Nov. 10, 2010, the entire content of which are hereby incorporated by reference.

BACKGROUND OF THE INVENTION

1. Field of the Invention

The present invention relates to a wireless communication device and a wireless communication system that perform wireless communication of control data for remotely controlling an external device.

2. Description of the Related Art

Generally, when a surgical operation is performed, a surgical operation system including a plurality of medical device groups in which a medical device corresponding to a purpose is mounted on a cart is used. The medical device group is freely arranged according to the kind of a surgical operation.

During the surgical operation, some of the medical devices are operated through remote control by a remote controller. Many remote controllers transmit control data to the medical devices through infrared communication.

For example, in Japanese Unexamined Patent Application, First Publication No. 2003-245286, a method of increasing an infrared amount through an infrared adapter and transmitting control data to a distant medical device is disclosed.

In Published Japanese Translation No. 2008-519501 of the PCT International Publication, the use of a remote controller using wireless technology (radio waves) of which a communication distance is long is shown.

Also, in Japanese Unexamined Patent Application, First Publication No. H7-147697, a method of preventing a collision by performing wave detection before transmission in communication between remote controllers is disclosed.

With the sophistication of a surgical operation, the number of medical device groups to be simultaneously used is increasing and arrangements of the medical device groups in a wide range are increasing. Further, cases in which image data such as endoscope images is communicated by wireless technology (radio waves) and displayed on monitors of other medical device groups are also increasing. Also, a device such as an electric scalpel, which generates electromagnetic noise in operation, is also frequently used. That is, cases in which the medical device groups are distributed and arranged in a wide range and devices that use radio waves or devices that generate radio waves are used are increasing.

SUMMARY

The present invention provides a wireless communication device and a wireless communication system capable of successfully performing communication of control data.

A wireless communication device may include: a wireless communication unit configured to perform wireless communication using radio waves belonging to a predetermined radio wave band between a first external device and a second external device; a proximity communication unit configured to perform proximity communication with a control terminal; and a control unit configured to cause control data, which indicates an instruction for the first external device, received from the control terminal via the proximity communication unit to be transmitted to the first external device via the wireless communication unit, the control unit adjusting a transmission timing of the control data or the data when causing the control data to be transmitted to the first external device while the first external device or the wireless communication unit sequentially transmits data to the second external device.

A wireless communication device may include: a wireless communication unit configured to perform wireless communication using radio waves belonging to a predetermined radio wave band with an external device; a proximity communication unit configured to perform proximity communication with a control terminal; and a control unit configured to cause control data, which indicates an instruction for the external device, received from the control terminal via the proximity communication unit to be transmitted to the external device via the wireless communication unit, the control unit adjusting a transmission timing of the control data based on an operation state of equipment that emits the radio waves belonging to a predetermined frequency band or transmitting an instruction for changing the operation state of the equipment to the equipment.

When causing the control data to be transmitted to the first external device while the first external device or the wireless communication unit sequentially transmits image data to the second external device, the control unit may adjust the transmission timing of the control data to a timing different from that of a predetermined wireless transmission period of the image data.

The wireless communication unit may have a function of performing wireless communication of image data with the first external device, and transmits the control data to the first external device using the function.

The control unit may adjust the transmission timing of the control data to a timing at which generation of electromagnetic noise by the equipment is determined to be small.

The external device may have the equipment individually having priority. The control data may include identifier (ID) information allocated to each piece of equipment and instruction information for an instruction for an operation of the equipment. A storage unit configured to store equipment information in which the ID information is associated with the priority may be further included. The control unit may identify the priority of the equipment of an object to be controlled based on the ID information and the equipment information included in the control data, determine equipment of which an operation state is changed based on the identified priority and the priority of each piece of equipment indicated by the equipment information, and transmit an instruction for changing the operation state of the equipment to the equipment.

The wireless communication unit may have a function of performing wireless communication of image data with the external device, and transmits the control data to the external device using the function.

A wireless communication system may include: a wireless communication device including: a first wireless communication unit configured to perform wireless communication using radio waves belonging to a predetermined radio wave band between a first external device and a second external device; a first proximity communication unit configured to perform proximity communication with a control terminal; and a first control unit, which is a control unit configured to cause control data, which indicates an instruction for the first external device, received from the control terminal via the first proximity communication unit to be transmitted to the first external device via the first wireless communication unit, the first control unit adjusting a transmission timing of the control data or the data when causing the control data to be transmitted to the first external device while the first external device or the wireless communication unit sequentially transmits data to the second external device; the control terminal including: a generation unit configured to generate the control data; and a second proximity communication unit configured to perform proximity communication with the wireless communication device; and the first external device including: a second wireless communication unit configured to perform wireless communication using the radio waves belonging to the predetermined radio wave band between the second external device and the wireless communication device; and a second control unit configured to perform control based on the control data received from the wireless communication device via the second communication unit.

A wireless communication system may include: a wireless communication device including: a first wireless communication unit configured to perform wireless communication using radio waves belonging to a predetermined radio wave band with an external device; a first proximity communication unit configured to perform proximity communication with a control terminal; and a first control unit, which is a control unit configured to cause control data, which indicates an instruction for the external device, received from the control terminal via the first proximity communication unit to be transmitted to the external device via the first wireless communication unit, the first control unit adjusting a transmission timing of the control data based on an operation state of equipment to emit the radio waves belonging to a predetermined frequency band or transmitting an instruction to change the operation state of the equipment to the equipment; the control terminal including: a generation unit configured to generate the control data; and a second proximity communication unit configured to perform proximity communication with the wireless communication device; and the external device including: a second wireless communication unit configured to perform wireless communication using the radio waves belonging to the predetermined radio wave band with the wireless communication device; and a second control unit configured to perform control based on the control data received from the wireless communication device via the second communication unit.

The control data may include ID information allocated to each piece of equipment of an object to be controlled and instruction information for an instruction for an operation of the equipment. The control terminal may include a reading unit configured to read the ID information from a display screen of an image display device having an information transmission function of optically transmitting the ID information using part of the display screen on which an image is displayed. The generation unit may generate the control data using the ID information read from the display screen.

A wireless communication device may include: a wireless communication unit configured to perform wireless communication using radio waves belonging to a predetermined radio wave band between a first external device and a second external device; a proximity communication unit configured to perform proximity communication with a control terminal; and a control unit configured to adjust a transmission timing of the control data to a timing different from that of a predetermined wireless transmission period of image data when causing control data, which indicates an instruction for the first external device, received from the control terminal via the proximity communication unit to be transmitted to the first external device via the wireless communication unit and when causing the control data to be transmitted to the first external device while the first external device or the wireless communication unit sequentially transmits image data to the second external device.

The control unit may adjust the transmission timing of the control data to within a blanking period of the wireless communication of the image data.

BRIEF DESCRIPTION OF THE DRAWINGS

FIG. 6 is a reference diagram illustrating content of a system state table in the first preferred embodiment of the present invention.

FIG. 7 is a reference diagram illustrating content of a control data transmission waiting table in the first preferred embodiment of the present invention.

FIG. 8 is a timing chart of wireless communication of control data in the first preferred embodiment of the present invention.

FIG. 15 is a reference diagram illustrating content of a system state table in the second preferred embodiment of the present invention.

FIG. 16 is a timing chart of wireless communication of control data in the second preferred embodiment of the present invention.

DESCRIPTION OF THE PREFERRED EMBODIMENTS

Hereinafter, preferred embodiments of the present invention will be described with reference to the drawings. However, the present invention is not limited to the following preferred embodiments. For example, components of the preferred embodiments may be appropriately combined.

First Preferred Embodiment

First, the first preferred embodiment of the present invention will be described. In the first preferred embodiment, an example in which the present invention is applied to a remote control system (wireless communication system) having medical device groups (external devices) configured on three carts will be described.

Figure 1:
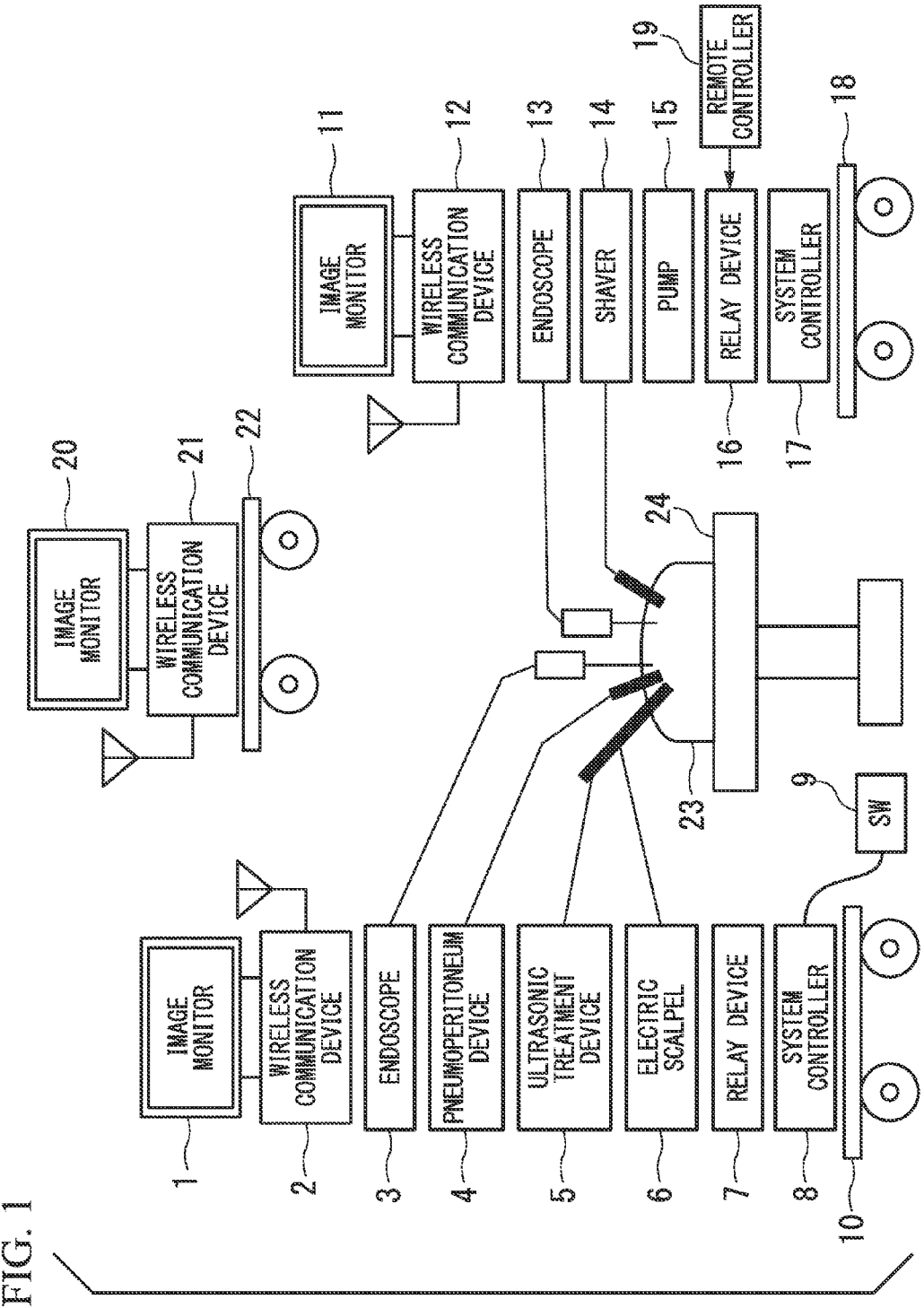
FIG. 1 is a block diagram illustrating a configuration of a remote control system in accordance with a first preferred embodiment of the present invention.

Using FIGS. 1 and 2, a configuration of the remote control system will be described. FIG. 1 illustrates the configuration of the remote control system in accordance with the first preferred embodiment.

On a cart 10, an image monitor 1, which displays an endoscope image or various control screens, a wireless communication device 2, which performs communication of image data and control data, an endoscope 3, a pneumoperitoneum device 4, an ultrasonic treatment device 5, an electric scalpel 6, a relay device 7, a system controller 8, and a foot switch 9 are mounted. The equipment on the cart 10 constitutes an external device in a wireless communication system of the present invention.

On a cart 18, an image monitor 11, which displays an endoscope image or various control screens, a wireless communication device 12, which performs communication of image data or control data, an endoscope 13, a shaver 14, a pump 15, a relay device 16, and a system controller 17 are mounted. The equipment on the cart 18 constitutes an external device (a first external device) in the wireless communication system of the present invention.

A remote controller 19 for remote control of each medical device is in the vicinity of the cart 18, and is in a state in which a signal from the remote controller 19 is transmitted only to the relay device 16 through infrared communication. Although the remote controller 19 is in the vicinity of the cart 18 in FIG. 1, a signal from the remote controller 19 is transmitted only to the relay device 7 on the cart 10 when the remote controller 19 is in the vicinity of the cart 10.

An image monitor 20 and a wireless communication device 21 are mounted on a cart 22, and the image monitor 20 displays an image received by the wireless communication device 21. The equipment on the cart 22 constitutes an external device (a second external device) in the wireless communication system of the present invention.

A patient 23 is placed on a patient bed 24 and a probe from a medical device such as an endoscope is installed thereon.

Because the endoscope, the pneumoperitoneum device, the ultrasonic treatment device, the electric scalpel, the shaver, and the pump in the drawing are known medical devices and will be described as having known functions even in the first preferred embodiment, a further description thereof is omitted here.

The foot switch 9 is connected to the system controller 8, and controls an output of the ultrasonic treatment device 5 or the electric scalpel 6. By switching an operation state of the foot switch 9, switching of whether to control the ultrasonic treatment device 5 or the electric scalpel 6 is configured to be performed from the remote controller 19.

The wireless communication device, the relay device, the system controller, and the remote controller will be described later.

Figure 2:
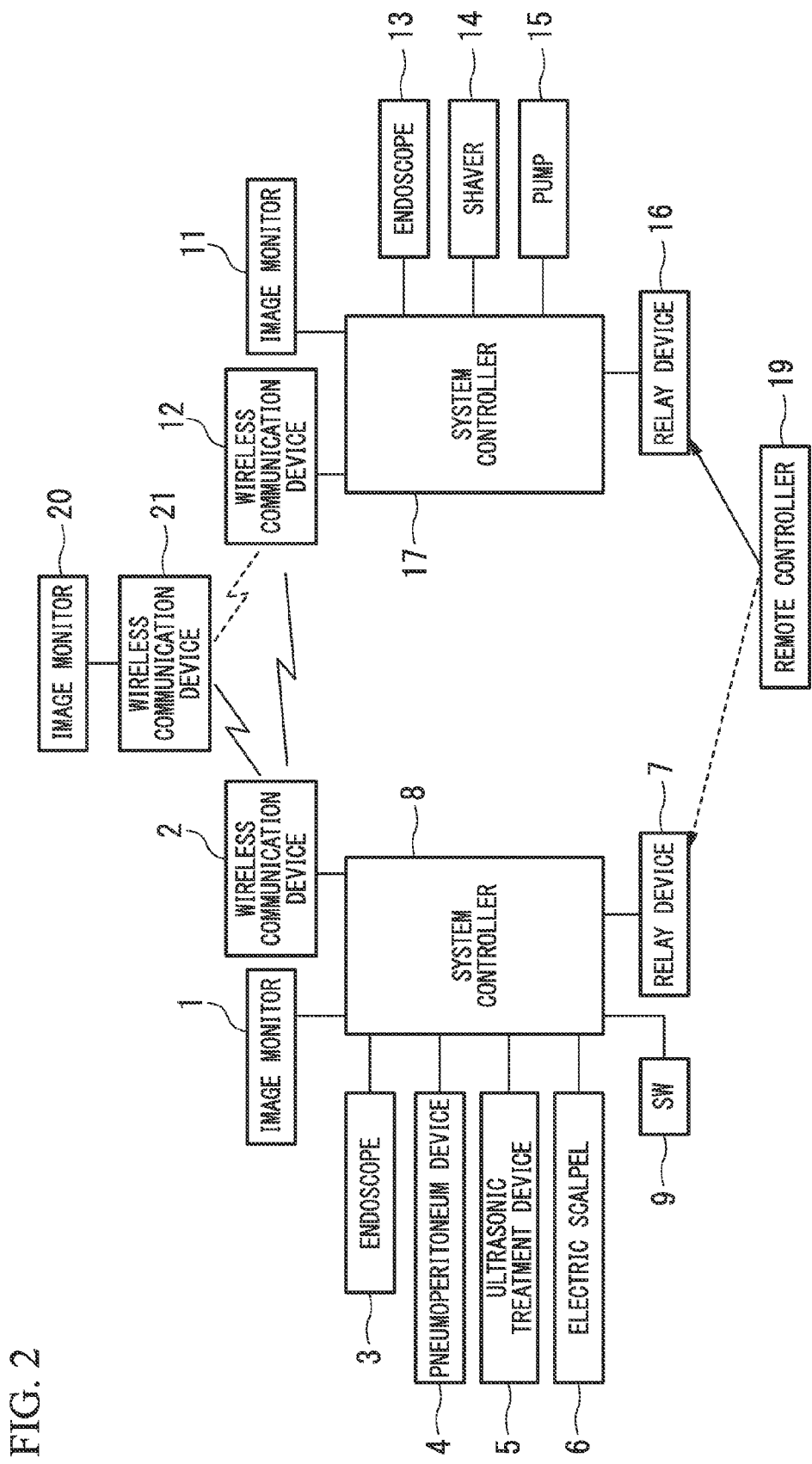
FIG. 2 is a block diagram illustrating a connection relationship between medical devices provided in the remote control system in accordance with the first preferred embodiment of the present invention.

FIG. 2 is a block diagram illustrating a connection relationship between medical devices provided in the remote control system. As illustrated, each device (equipment) mounted on the cart 10 is connected to the system controller 8 and the system controller 8 recognizes an operation state of each device. Likewise, each device (equipment) mounted on the cart 18 is connected to the system controller 17, and the system controller 17 recognizes an operation state of each device.

FIG. 2 illustrates a state in which a signal output by the remote controller 19 is transmitted only to the relay device 16. Based on information from the system controller 8, the relay device 7 recognizes the operation state of each device mounted on the cart 10, exchanges information with the relay device 16 through wireless communication via the wireless communication device 2 and the wireless communication device 12, and also recognizes the operation state of each device mounted on the cart 18. Likewise, based on information from the system controller 17, the relay device 16 recognizes the operation state of each device mounted on the cart 18, exchanges information with the relay device 7 through wireless communication via the wireless communication device 2 and the wireless communication device 12, and also recognizes the operation state of each device mounted on the cart 10. A method in which the above-described relay devices recognize the operation state of each device will be described in detail using FIGS. 5 to 11 later.

The wireless communication device 2 of the cart 10, the wireless communication device 12 of the cart 18, and the wireless communication device 21 of the cart 22 perform wireless communication belonging to a predetermined radio wave band (frequency band). These wireless communication devices have an image communication function. In FIG. 2, the wireless communication device 2 of the cart 10 and the wireless communication device 21 of the cart 22 perform wireless communication of image data. Also, the wireless communication device 2 of the cart 10 and the wireless communication device 12 of the cart 18 perform wireless communication of control data for controlling the operation of each device using the image communication function.

Next, configurations of the remote controller 19 and the relay devices 7 and 16 will be described using FIGS. 3 to 5. In the following description, a state in which a signal from the remote controller 19 is transmitted only to the relay device 16 is assumed as illustrated in FIGS. 1 and 2.

Figure 3:
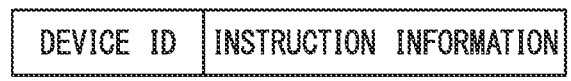
FIG. 3 is a reference diagram illustrating a structure of control data in the first preferred embodiment of the present invention.

FIG. 3 illustrates a structure of control data (a control command) transmitted from the remote controller 19. As illustrated, the control data includes a device identifier (ID) (ID information) indicating an ID of a device of an object to be controlled and instruction information indicating instruction content (control content) for the device of the object to be controlled.

Figure 4:
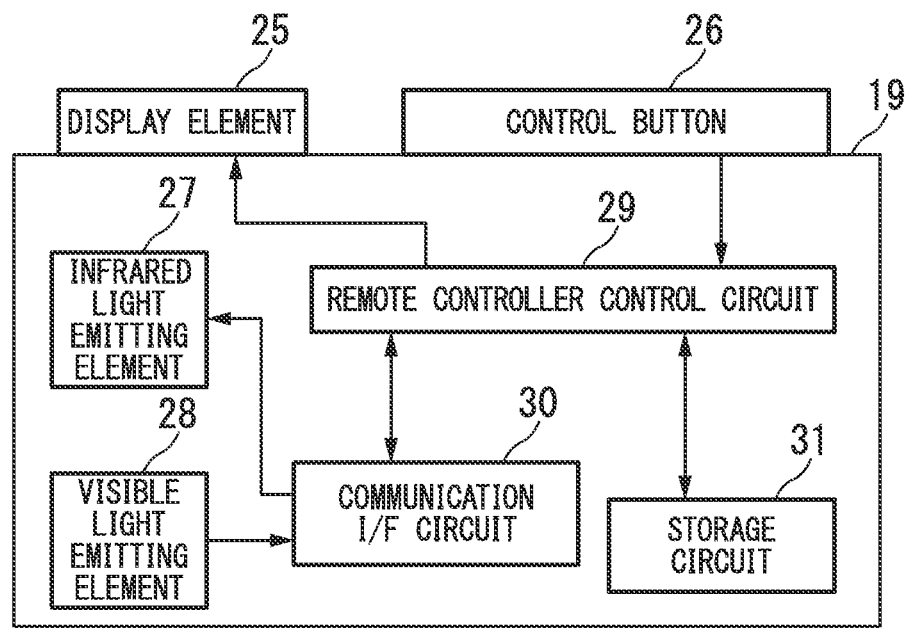
FIG. 4 is a block diagram illustrating a configuration of a remote controller provided in the remote control system in accordance with the first preferred embodiment of the present invention.

FIG. 4 illustrates the configuration of the remote controller 19. The remote controller 19 includes an infrared light emitting element 27, a visible light receiving element 28, a communication interface (I/F) circuit 30, a control button 26, a display element 25, a storage circuit 31, and a remote controller control circuit 29.

The infrared light emitting element 27 transmits control data through infrared communication. Because infrared light is used, it is difficult for communication of the remote controller 19 and the relay devices 7 and 16 to be affected by electromagnetic noise generated by the electric scalpel 6 or the like. Although an example in which the remote controller 19 performs infrared communication is shown in the preferred embodiment of the present invention, it is only necessary that communication to be performed by the remote controller 19 be proximity communication (near field communication) in which communication is possible only in the vicinity of the relay device, and ultrasonic waves or the like may be used instead of infrared light.

The visible light receiving element 28 receives a device ID of each device in optical communication via an image monitor. The reception of the device ID according to the optical communication will be described in detail using FIG. 12 later.

The communication I/F circuit 30 performs communication using the infrared light emitting element 27 and the visible light receiving element 28. The control button 26 receives an operation input for instructing to operate the remote controller 19. The display element 25 displays an operation state of the remote controller 19. The storage circuit 31 stores the device ID received in the optical communication. The remote controller control circuit 29 controls the overall operation of the remote controller 19.

When an operator inputs desired instruction content (control content) by operating the control button 26, the remote controller control circuit 29 generates instruction information by analyzing the instruction content, displays a result on the display element 25, and generates control data by adding the device ID stored in the storage circuit 31 to the instruction information. The control data is transmitted by infrared light via the communication I/F circuit 30 and the infrared light emitting element 27, and received by the relay device in the vicinity thereof.

Figure 5:
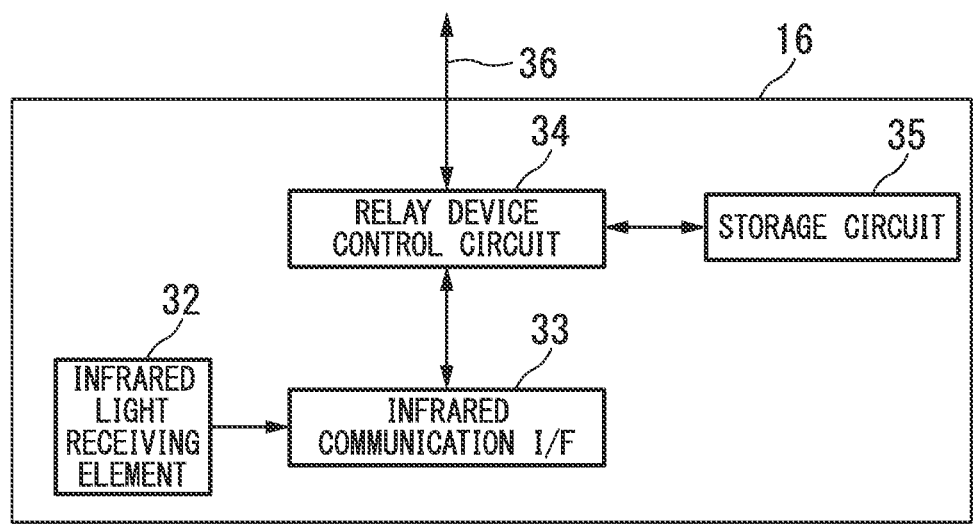
FIG. 5 is a block diagram illustrating a configuration of a relay device provided in the remote control system in accordance with the first preferred embodiment of the present invention.

FIG. 5 illustrates the configuration of the relay device 16. The relay device 16 includes an infrared light receiving element 32, an infrared I/F circuit 33, a relay device control circuit 34, and a storage circuit 35.

The infrared light receiving element 32 receives control data from the remote controller 19 through infrared communication. The infrared I/F circuit 33 processes a signal from the infrared light receiving element 32 and transmits the processed signal to the relay device control circuit 34. The relay device control circuit 34 controls the entire relay device 16. The storage circuit 35 stores a system state table in which a list of states of each device (equipment) on the cart 10 and states of each device (equipment) on the cart 18 is shown and a control data transmission waiting table in which a list of control data waiting for transmission to the relay device is shown. Also, the relay device 7 is connected to the system controller 17 via a relay device input/output signal 36 from the relay device control circuit 34. Furthermore, the configuration of the relay device 7 is also the same as that of the relay device 16.

Upon receiving control data from the remote controller 19, the relay device 16 notifies the system controller to which a device of an object to be controlled is connected of a control command based on a device ID within the control data. The system controller receiving the control command appropriately controls the device to be controlled based on the control command.

For example, when the control command is a command for the shaver 14, the relay device 16 directly notifies the system controller 17 of the control command based on the received control data because the shaver 14 is connected to the system controller 17 of the same cart 18 as that of the relay device 16. Also, when the control command is a command for the pneumoperitoneum device 4, the control data is transmitted to the relay device 7 in wireless communication via the wireless communication devices 2 and 12 and the relay device 7 notifies the system controller 8 of the control command because the pneumoperitoneum device 4 is connected to the system controller 8 of the cart 10 on which the relay device 7 is placed. These procedures will be described using FIGS. 8 to 11 later.

Next, the system state table and the control data transmission waiting table to be used by the relay device will be described using FIGS. 6 and 7. FIG. 6 is an example of the system state table. The system state table is a table to be used for a determination of whether to transmit control data from the remote controller 19 through wireless communication and a decision of a start timing of the wireless communication to be performed by recognizing the operation state of the device on the cart on which the relay device within the remote control system is mounted.

As illustrated in FIG. 6, the system state table records a type of device mounted on each cart, a device ID, an operation state, and the presence/absence of electromagnetic noise, which is generated when the device is in operation. For example, in FIG. 6, for the electric scalpel 6 mounted on the cart 10, the device ID: SG-001, the operation state: in operation, and the electromagnetic noise generated when the device is in operation: present are registered. This shows that wireless communication of control data from the remote controller 19 is not possible because electromagnetic noise is generated when the electric scalpel 6 is in operation.

FIG. 7 is an example of a control data transmission waiting table to be used by the relay device. The control data transmission waiting table is a table in which control data, which should be transmitted to the relay device of another cart through wireless communication, among control data received from the remote controller 19 is summarized. As illustrated in FIG. 7, the control data transmission waiting table records an ID of a relay device serving as a transmission destination, a type of device serving as an object to be controlled, a device ID, control content, and a reception time based on reception of control data. In FIG. 7, an example in which a command for changing a connection destination of the foot switch from the current electric scalpel 6 to the ultrasonic treatment device 5 and a command for changing a flow rate of the pneumoperitoneum device 4 are registered is illustrated.

Next, a procedure of transmitting control data from the remote controller 19 in wireless communication will be described using FIGS. 8 to 11. An example in which an image of the endoscope 3 is being communicated to the wireless communication device 21 connected to the image monitor 20 via the wireless communication device 2 and the wireless communication device 21, control content (a change in a connection destination of the foot switch and a flow rate change in the pneumoperitoneum device) illustrated in FIG. 7 from the remote controller 19 is indicated to the relay device 16, and the electric scalpel 6 is in an initial operation and then is stopped is shown in the present invention.

FIG. 8 illustrates a state in which control data is wirelessly transmitted in the above-described procedure. In FIG. 8, the electric scalpel 6 is operated until a time t6 and then stopped. The wireless communication device 2 periodically transmits the image of the endoscope 3. For example, when one frame includes 60 images, a transmission cycle is 16.7 ms. In the drawing, a period between times t1 and t5 becomes 16.7 ms. A period of times t4 to t5 is a blanking period in which no image data is transmitted, and control data is wirelessly communicated using the above-described period.

Because electromagnetic noise is generated when the electric scalpel 6 is in operation, content of wireless communication may not be necessarily accurately transmitted. Although a disturbance is allowed even when the disturbance occurs on a screen under the influence of electromagnetic noise because image data is continuously transmitted, wireless communication of control data is not performed in a period in which electromagnetic noise is generated because an error of control data is likely to cause a serious problem.

In FIG. 8, control data indicating a control command (a flow rate change in the pneumoperitoneum device) from the remote controller 19 is transmitted to the relay device 16 during a period of times t2 to t3. The control data received by the relay device 16 is added to the control data transmission waiting table. At this time, because wireless transmission is not performed when the electric scalpel 6 is in operation, new control data is added after control data indicating a previously indicated change command of a connection destination of the foot switch as illustrated in FIG. 7.

In the blanking period of the times t4 to t5, wireless transmission is not performed because the electric scalpel 6 is in operation. In an initial blanking period after the electric scalpel 6 has been stopped, the system state table is transmitted from the relay device 7 to which the electric scalpel 6 is connected to the relay device 16, and notification of an operation stop of the electric scalpel 6 is provided (times t7 to t8). According to this notification, the stop of the electric scalpel 6 is checked in the relay device 16. As a result, the content of the control data transmission waiting table is transmitted in the next blanking period (times t9 to t10).

Although a procedure in which the wireless communication device 2 transmits image data to the wireless communication device 21 has been described above, a procedure in which the wireless communication device 12 transmits image data to the wireless communication device 21 is also the same, and the relay device 16 controls a transmission timing of control data so that the wireless communication device 21 transmits the control data in the blanking period after the stop of the electric scalpel 6.

Figure 9:
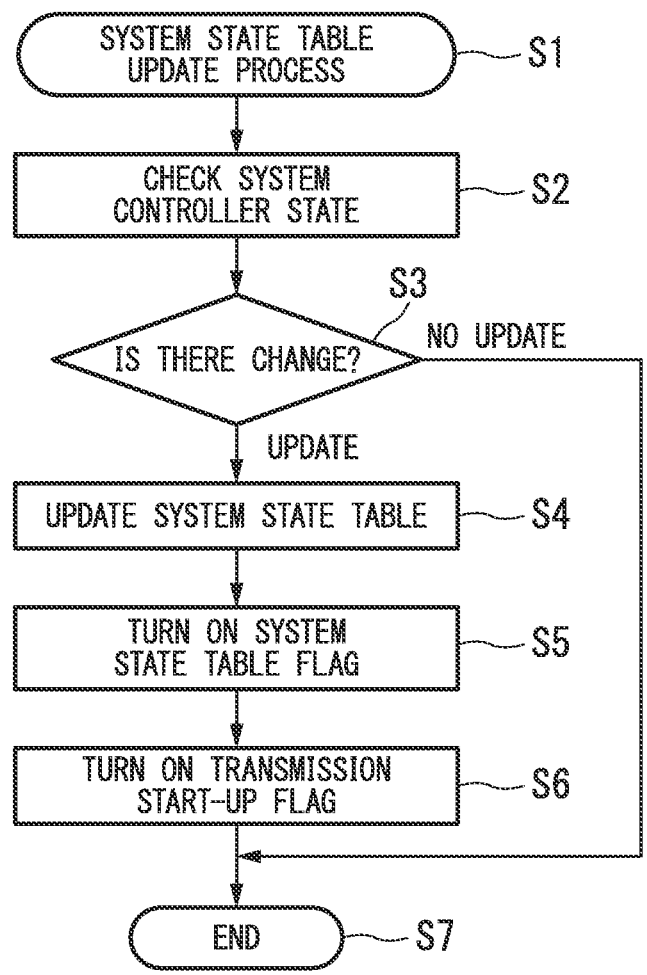
FIG. 9 is a flowchart illustrating a procedure of an operation of a relay device provided in the remote control system in accordance with the first preferred embodiment of the present invention.
Figure 10:
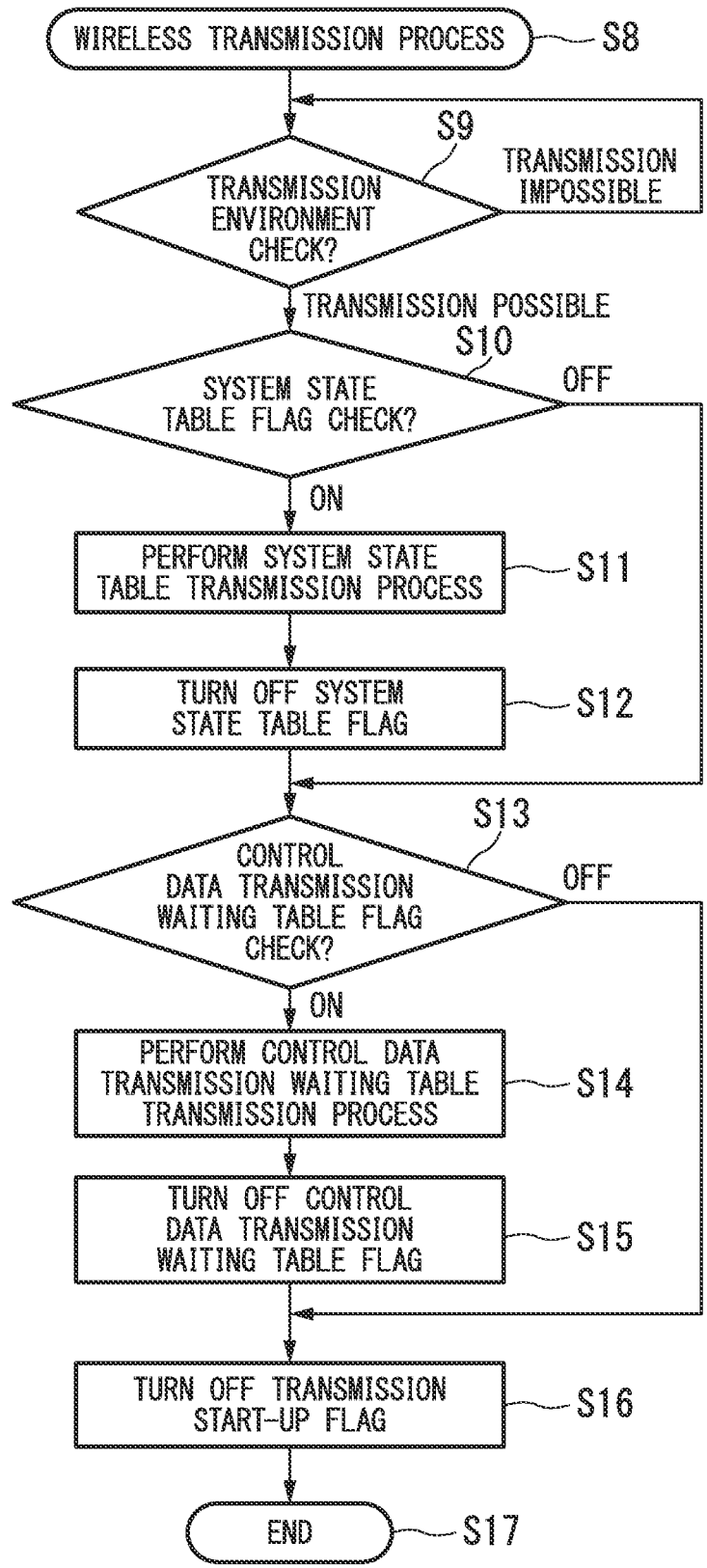
FIG. 10 is a flowchart illustrating a procedure of an operation of the relay device provided in the remote control system in accordance with the first preferred embodiment of the present invention.
Figure 11:
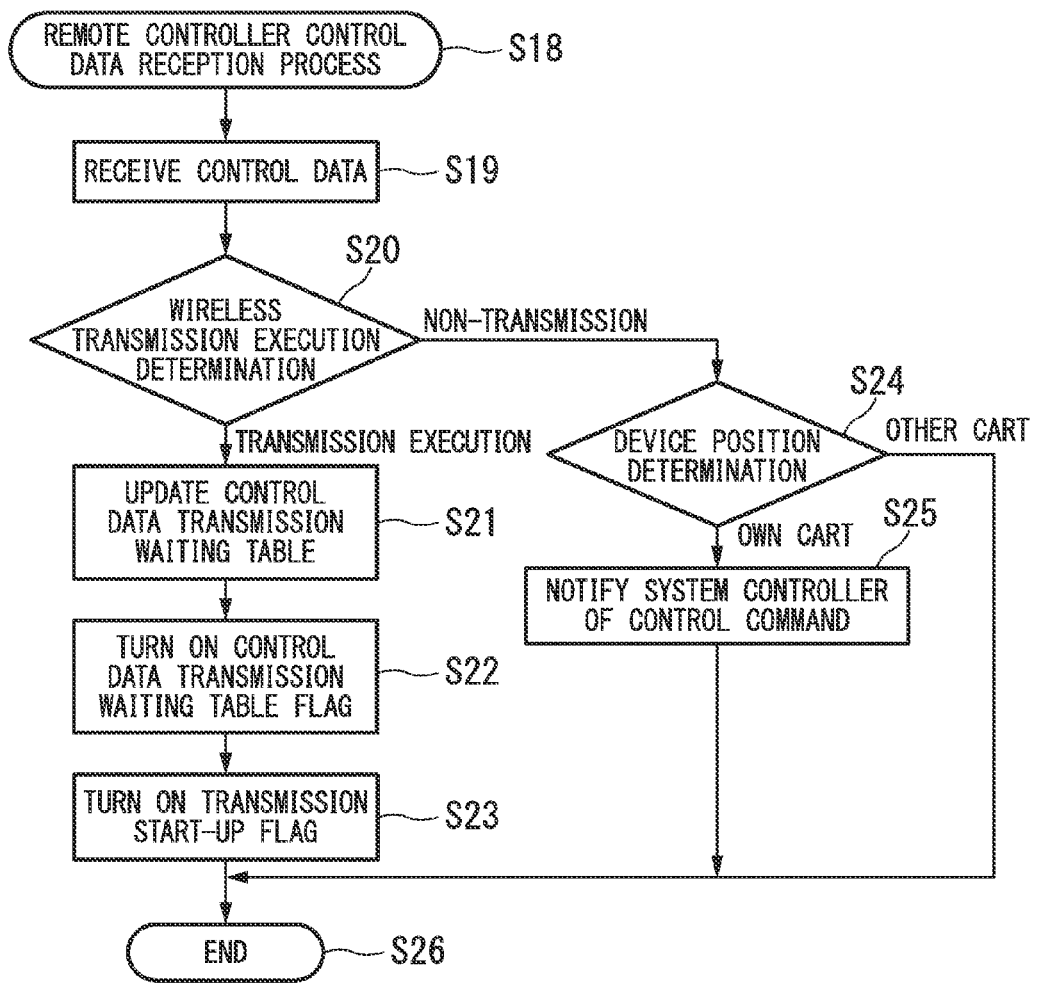
FIG. 11 is a flowchart illustrating a procedure of an operation of the relay device provided in the remote control system in accordance with the first preferred embodiment of the present invention.

Next, the operation of the relay device will be described using FIGS. 9 to 11. The flowcharts of FIGS. 9 to 11 are common in the relay device 7 and the relay device 16. Also, processes illustrated in FIGS. 9 to 11 are executed by software under operating system (OS) management, and separate software under the OS management is executed after the end of the processes.

FIG. 9 illustrates a system state table update process S1. The system state table update process S1 is a process in which the relay device periodically observes a state of each device connected to the system controller via its own connected system controller and updates the system state table.

In the system state table update process S1, the relay device control circuit 34 initially checks the state of each device via the system controller (S2). Subsequently, the relay device control circuit 34 compares content of the system state table stored in the storage circuit 35 to the state of each device of notification from the system controller (S3). If there is no change in the state of each device, the system state table update process S1 ends (S7). Also, if there is a change in the state of each device, the relay device control circuit 34 performs the update S4 of the system state table, a system state table flag is turned ON (S5), a transmission start-up flag is turned ON (S6), and the system state table update process S1 ends (S7).

The system state table flag is a flag indicating that the system state table has been updated, and the transmission start-up flag is a flag for requesting the start-up of a wireless transmission process S8 as will be described next. When the operation of the electric scalpel 6 has been stopped, the update (S4) of the system state table is performed in the relay device 7 and then the system stable table flag and the transmission start-up flag are turned ON (S5 and S6).

FIG. 10 illustrates the wireless transmission process S8. The wireless transmission process S8 is a process of transmitting content of the system state table and the control data transmission waiting table. When the transmission start-up flag is turned ON, the wireless transmission process S8 is started up. When the system state table flag is turned ON, the system state table updated in the system state table update process S1 is transmitted. When the control data transmission waiting table flag is turned ON, content of the control data transmission waiting table is transmitted.

In the wireless transmission process S8, the relay device control circuit 34 examines the system state table in a transmission environment check S9, and determines whether transmission is possible. When the device for which electromagnetic noise: present is registered is in operation, the relay device control circuit 34 iterates the transmission environment check S9 by determining that the transmission is not possible. When the device for which the electromagnetic noise: present is registered is not in operation, the relay device control circuit 34 checks the system state table flag (S10). When the system state table flag is turned ON, the relay device control circuit 34 executes a system state table transmission process S11 and a system state table flag OFF process S12, and then executes a control data transmission waiting table flag check S13. When the system state table flag is turned OFF, the relay device control circuit 34 directly executes the control data transmission waiting table flag check S13.

In the system state table transmission process S11, the system state table updated in the system state table update process S1 is transmitted. In the system state table transmission process S11, the relay device control circuit 34 outputs the system state table to the wireless communication device via the system controller, and the wireless communication device transmits the system state table to another wireless communication device using the next blanking period. The system state table received by another wireless communication device is output to the relay device via the system controller. In the relay device, the relay device control circuit 34 updates the system state table stored in the storage circuit 35.

After the system state table transmission process S11 the relay device control circuit 34 turns OFF the system state table flag (S12).

In the control data transmission waiting table flag check S13, the relay device control circuit 34 checks the control data transmission waiting table flag. When the control data transmission waiting table flag is turned ON, the relay device control circuit 34 executes a control data transmission waiting table transmission process S14 and a control data transmission waiting table flag OFF process S15, and then executes a transmission start-up flag OFF process S16.

In the control data transmission waiting table transmission process S14, the relay device control circuit 34 outputs control data to the wireless communication device via the system controller, and transmits the control data to another wireless communication device using the next blanking period. After the control data transmission waiting table transmission process S14, the relay device control circuit 34 turns OFF the control data transmission waiting table flag and the transmission start-up flag (S15 and S16), and ends the wireless transmission process S8.

When the control data transmission waiting table flag is turned OFF, the relay device control circuit 34 directly executes the transmission start-up flag OFF process S16.

After the transmission start-up flag OFF process S16, the wireless transmission process S8 ends (S17).

FIG. 11 illustrates a remote controller control data reception process S18. The remote controller control data reception process S18 is a process to be performed upon receipt of control data from the remote controller 19. Upon receipt of the control data from the remote controller 19, the relay device control circuit 34 starts up the remote controller control data reception process S18. In the remote controller control data reception process S18, the relay device control circuit 34 initially performs reception S19 of the control data, and subsequently makes a wireless transmission execution determination S20.

In the wireless transmission execution determination S20, the relay device control circuit 34 makes a device position determination S24 when a device of an object to be controlled specified from a device ID within control data is mounted on the same cart as its own cart and communication from the remote controller 19 and when communication from the remote controller 19 arrives at both the relay device 7 and the relay device 16. Otherwise, the update S21 of the control data transmission waiting table is executed. Furthermore, a determination of a relay device at which communication from the remote controller 19 arrives is made by determining whether operation states of all relay devices of the system state table illustrated in FIG. 6 are "in remote controller connection."

In the device position determination S24, the relay device control circuit 34 determines a device of an object to be controlled from a device ID within the control data. When the device of the object to be controlled is on the same cart as its own cart, the relay device control circuit 34 executes control command notification S25 to the system controller and ends the remote controller control data reception process S18 (S26). Otherwise, the relay device control circuit 34 immediately ends the remote controller control data reception process S18 (S26).

In the update S21 of the control data transmission waiting table, the relay device control circuit 34 adds control data received from the remote controller 19 to the control data transmission waiting table stored in the storage circuit 35. At this time, only latest control data is placed in the control data transmission waiting table based on a reception time for control data in which control content (for example, a flow rate change in the pneumoperitoneum device or the like) is redundant among control data for the same device.

After the update S21 of the control data transmission waiting table, the relay device control circuit 34 turns ON the control data transmission waiting table flag (S22), turns ON the transmission start-up flag (S23), and ends the remote controller control data reception process S18 (S26).

Next, an example of transmission of control data of the remote controller 19 in the wireless transmission process S8 will be described. In the case of an example illustrated in FIG. 8, in the relay device 16, the wireless transmission process S8 is started up through the remote controller control data reception process S18 performed when the electric scalpel 6 is in operation. However, until the system state table is transmitted from the relay device 7 and notification of the stop of the electric scalpel 6 is provided, communication is determined to be impossible through the transmission environment check S9 and transmission of the control data is awaited. When the system state table is updated in the notification from the relay device 7, transmission is determined to be possible in the transmission environment check S9 and a process from a system state table flag check S10 is executed.

In this case, because the system state table flag is turned OFF and the control data transmission waiting table flag is turned ON, the control data transmission waiting table transmission process S14 is performed, the control data transmission waiting table flag OFF process S15 is subsequently performed, and the wireless transmission process S8 ends (S17) after the transmission start-up flag OFF process S16. Through the above-described process, transmission of control data of the remote controller 19 is performed at a timing shown in times t9 to t10 of FIG. 8.

Because both the operation states of the relay device 7 and the relay device 16 of the system state table illustrated in FIG. 6 are in the remote controller connection when a position of the remote controller 19 is different from positions illustrated in FIGS. 1 and 2 and communication from the remote controller 19 reaches both the relay device 7 and the relay device 16, "non-transmission" is determined in a wireless transmission execution determination S20 in the relay device 16, "other cart" is determined in a device position determination S24, and the remote controller control data reception process S18 directly ends (S26). On the other hand, in the relay device 7, "non-transmission" is determined in the wireless transmission execution determination S20, "own cart" is determined in the device position determination S24, the control command notification S25 for the system controller 8 is executed, and then the remote controller control data reception process S18 ends (S26).

When the communication from the remote controller 19 reaches both the relay device 7 and the relay device 16 as described above, the system controller to which the device of the object to be controlled is connected is notified of a control command without performing wireless transmission.

Figure 12:
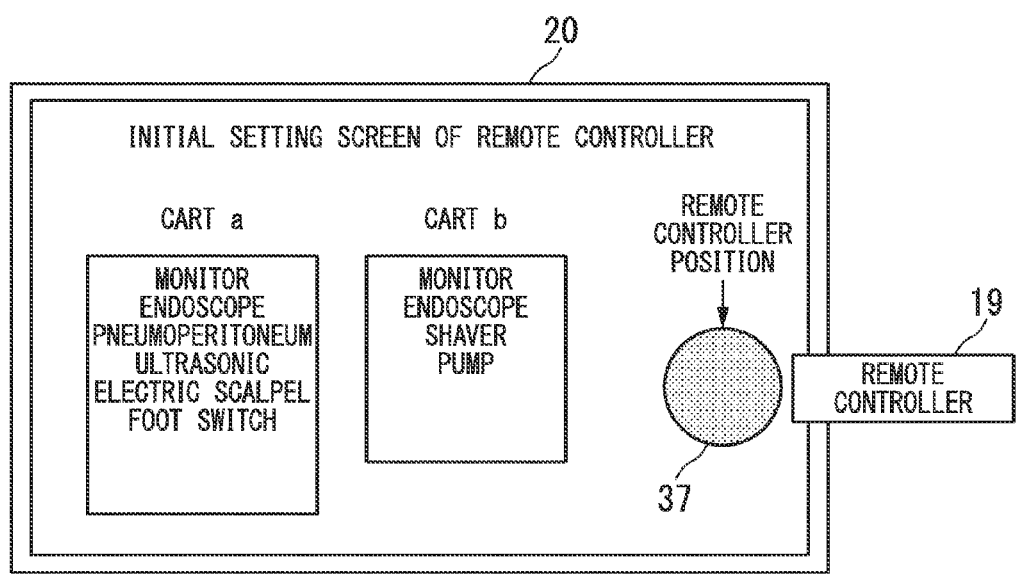
FIG. 12 is a reference diagram illustrating a display screen for an initial setting process of the remote controller in the first preferred embodiment of the present invention.

Next, an initial setting process of the remote controller 19 will be described. In the initial setting process of the remote controller 19, a process of setting a device ID of each medical device within the remote control system in the remote controller 19 is performed. FIG. 12 illustrates the case in which a screen for the initial setting process is displayed on the image monitor 20.

As illustrated, a name of a device to be remotely controlled by the remote controller 19 is displayed for each cart on the screen for the initial setting process. On the side of the screen, an ID communication point 37 for transmitting a device ID of each device in visible light communication to the remote controller 19 is arranged. The ID communication point 37 has a function of providing notification of the device ID in a change (blinking) in luminance and notifies the remote controller 19 of the device ID through the visible light receiving element 28 of the remote controller 19.

Each device ID is collected by the relay device of each cart via the system controller and stored as part of the system state table. During initial setting, data of a device ID is extracted from a desired relay device.

Although a display of the screen for the initial setting process is possible even in the image monitor 1 and the image monitor 11, an example in which a screen created by the system controller 8 is displayed on the image monitor 20 will be described in the present invention. In this case, the system controller 8 creates the screen for the initial setting process using the device ID stored in the system state table of the relay device 7. The created screen is displayed on the image monitor 20 via the wireless communication device 2 and the wireless communication device 21. Because a method of blinking a part within the monitor and transferring information in visible light communication according to a change in a blinking interval used in the first preferred embodiment is known, a detailed description thereof is omitted here.

As described above, according to the first preferred embodiment, communication of control data can be successfully performed by transmitting the control data at a timing at which other wireless communication or electromagnetic noise is not generated and a wireless communication state is good when the relay device wirelessly transmits the control data received from the remote controller 19 through infrared communication using a wireless communication device on its own cart. Also, in a system for wirelessly communicating and displaying image data, it is possible to provide a remote control system that reliably notifies a separated non-control device group of a control command by wirelessly transmitting control data at a timing at which a communication period of the image data is avoided.

When a device in which a large amount of electromagnetic noise is generated in operation such as an electric scalpel is in operation, it is difficult to perform wireless communication normally. Thus, normal communication can be performed without being affected by electromagnetic noise by monitoring an operation state of a device, which generates the electromagnetic noise, detecting a time point of an operation state in which the generation of the electromagnetic noise is small such as power OFF or operation interruption, and performing wireless communication of control data at the time point.

Also, the setting of the remote controller 19 can be performed by reading a device ID from an image display monitor and convenience is improved. Furthermore, because it is not necessary to newly prepare a wireless communication device for communication of control data by performing wireless communication of the control data using an image communication function, cost reduction is possible when the remote control system in accordance with the first preferred embodiment is configured.

Second Preferred Embodiment

Next, the second preferred embodiment of the present invention will be described. In the second preferred embodiment, the function of the relay device is mainly different from that of the first preferred embodiment. Specifically, the relay device of the second preferred embodiment has a wireless communication function and wireless communication is performed between relay devices. Also, priority is allocated to each medical device, and processing in the relay device changes according to priority of a medical device in operation upon receipt of control data from the remote controller 19.

Figure 13:
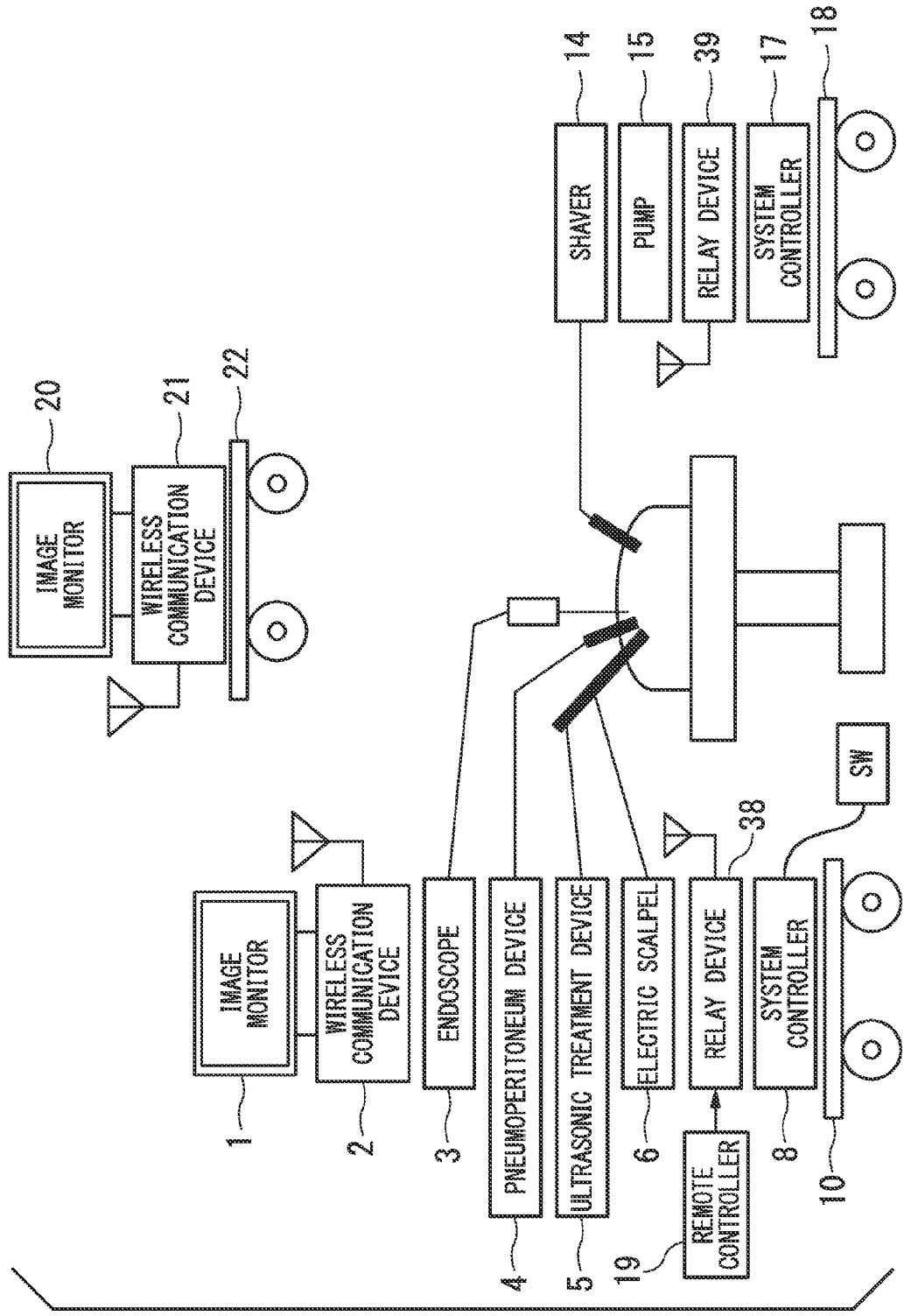
FIG. 13 is a block diagram illustrating a configuration of a remote control system in accordance with a second preferred embodiment of the present invention.

FIG. 13 illustrates a configuration of the remote control system in accordance with the second preferred embodiment. Comparing the remote control system in accordance with the second preferred embodiment to the remote control system in accordance with the first preferred embodiment, configurations of the relay device and the cart 18 are different.

The configuration of the cart 18 is a configuration in which the image monitor 11, the wireless communication device 12, and the endoscope 13 are removed from the configuration illustrated in FIG. 1. In the second preferred embodiment, no wireless communication device can be used for transmission of control data between the relay devices as in the first preferred embodiment because the wireless communication device 12 is not on the cart 18. Thus, the relay device 38 and the relay device 39 of this system are equipped with the wireless communication function, and wireless communication is directly performed between the relay devices.

Figure 14:
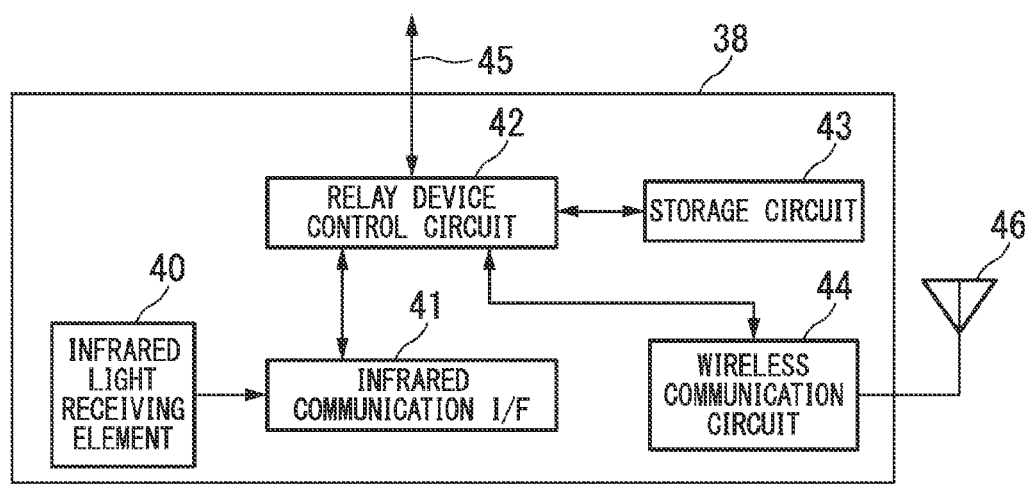
FIG. 14 is a block diagram illustrating a configuration of a relay device provided in the remote control system in accordance with the second preferred embodiment of the present invention.

FIG. 14 illustrates a configuration of the relay device 38 mounted on the cart 10. As illustrated, a wireless communication circuit 44 is connected to a relay device control circuit 42, and an antenna 46 is connected to the wireless communication circuit 44. Because an infrared light receiving element 40, an infrared I/F circuit 41, a relay device control circuit 42, and a storage circuit 43 are the same as the configurations described in the first preferred embodiment, description thereof is omitted. Furthermore, the relay device 39 also has the same configuration. Through the above-described configuration, it is possible to perform wireless communication between the relay device 38 and the relay device 39.

In the second preferred embodiment, unlike the first preferred embodiment, priority is allocated to each medical device within the remote control system. Although wireless communication between relay devices is necessary when a control command for a high-priority device is issued from the remote controller 19 during the operation of a low-priority device, a wirelessly communicable state is created and the wireless communication between the relay devices is performed by changing an operation state of the low-priority device when the low-priority device in operation generates noise that interferes with wireless communication. Furthermore, because a previously operated device is prioritized when priority is the same, the operation state is not changed.

FIG. 15 illustrates an example of the system state table of the second preferred embodiment. In the second preferred embodiment, priority of each device is added to the system state table described in the first preferred embodiment. As illustrated, priority of the system controller is highest priority 1. Thereafter, the priority is successively given to the electric scalpel: 2 and the ultrasonic treatment device: 3. Also, because the relay device of the second preferred embodiment is not the object to be controlled by the remote controller 19, no priority is assigned thereto. A command for various urgent processes (urgent stop and the like) is included in a command for the system controller of which priority is 1.

Furthermore, in the first preferred embodiment, an item of noise of the system state table is set to "absent" because a radio signal associated with the operation of the wireless communication device does not become noise by transmitting control data using a blanking period of wireless communication of image data. On the other hand, in the second preferred embodiment, the item of noise of the system state table is set to "present" because a radio signal associated with the operation of the wireless communication device becomes noise for wireless communication between the relay devices.

Next, the communication timing of control data will be described using FIG. 16. In the present invention, an example in which the remote controller 19 transmits control data for the shaver 14 to the relay device 38 will be described using the configuration illustrated in FIG. 13. At this time, it is assumed that the wireless communication device 2 is in a state in which image data is transmitted to the wireless communication device 21, and operation states of the other devices become states illustrated in FIG. 15.

FIG. 16 is a timing chart of communication of control data in the above-described states. When the relay device 38 has received control data from the remote controller 19, the relay device control circuit 42 of the relay device 38 compares priority of a control object device corresponding to a device ID within control data to priority of a device that generates noise in operation in the system state table. Because control data is transmitted to the shaver 14 in the present invention, priority "2" of the shaver 14 is compared to priority "7" of the wireless communication device 2 in operation.

Because the priority of the shaver 14 is higher than the priority of the wireless communication device 2 when the relay device 38 has received control data from the remote controller 19 at the illustrated timings (times t12 to t13), the relay device control circuit 42 of the relay device 38 notifies the system controller 8 of an operation stop command of the wireless communication device 2. An operation of the wireless communication device 2 is stopped through the system controller 8 receiving the notification (a time t14). Thereby, the wireless communication of image data to be originally performed until a time t17 is stopped at the time t14.

Subsequently, the relay device control circuit 42 transmits control data to the relay device 39 via the wireless communication circuit 44 and the antenna 46 (times t15 to t16). The relay device control circuit 42 of the relay device 39 notifies the system controller 17 of a control command based on the received control data. The system controller 17 controls the shaver 14 based on the control command of the notification. Thereafter, the operation of the wireless communication device 2 is resumed (from a time t18). Through the above-described procedure, the control data from the remote controller 19 is transmitted to the shaver 14 via the relay device 38 and the relay device 39.

The initial setting process of the remote controller 19 in the second preferred embodiment is performed using data from a detachable universal serial bus (USB) memory attached to the remote controller 19 differently from the first preferred embodiment. The setting of a device ID of each medical device within the remote control system for the USB memory is performed by attaching the USB memory to the relay device. Because a method of setting information via the USB memory is known, a detailed description thereof is omitted here.

As described above, according to the second preferred embodiment, communication of control data can be successfully performed by transmitting the control data at a timing at which other wireless communication or electromagnetic noise is not generated and a wireless communication state is good when the relay device wirelessly transmits the control data received from the remote controller 19 through infrared communication using its own wireless communication device.

Also, when control data for a high-priority device is transmitted from the remote controller 19, a device that generates a large amount of noise according to an operation is in operation in a medical device group to which a relay device receiving control data from the remote controller 19 belongs, and the priority of the device is lower than the priority of a medical device to receive a control command, it is possible to transmit the control data after reducing the noise by stopping the device in operation. Thus, it is possible to transmit control data for a high-priority medical device early and reliably.

In accordance with the present invention, when a wireless communication device performs transmission of control data from a control terminal, a transmission timing of data such as control data or image data is adjusted. Alternatively, communication of the control data can be successfully performed because the control data can be transmitted at a timing at which radio waves having an influence on the transmission of the control data are not generated by transmitting an instruction for changing an operation state of equipment, which emits radio waves belonging to a predetermined frequency band, to the equipment.

Although the preferred embodiments of the present invention have been described above with reference to the drawings, specific configurations are not limited to the preferred embodiments, and designs can also be made without departing from the scope of the present invention.

The present invention can be widely applied to a wireless communication device and a wireless communication system that perform wireless communication of control data for remotely controlling an external device.

What is claimed is:

1. A wireless communication device comprising:
   a wireless communication unit configured to perform wireless communication using radio waves belonging to a predetermined radio wave band between a first external device and a second external device;
   a proximity communication unit configured to perform proximity communication with a control terminal; and
   a control unit configured to adjust a transmission timing of the control data to a timing different from that of a predetermined wireless transmission period of image data when causing control data, which indicates an instruction for the first external device, received from the control terminal via the proximity communication unit to be transmitted to the first external device via the wireless communication unit and when causing the control data to be transmitted to the first external device while the first external device or the wireless communication unit sequentially transmits image data to the second external device,
   wherein the control unit adjusts the transmission timing of the control data to within a blanking period of the wireless communication of the image data.

2. The wireless communication device according to claim 1, wherein the wireless communication unit has a function of performing wireless communication of image data with the first external device, and transmits the control data to the first external device using the function.

3. A wireless communication device comprising:
   a wireless communication unit configured to perform wireless communication using radio waves belonging to a predetermined radio wave band with an external device;
   a proximity communication unit configured to perform proximity communication with a control terminal; and
   a control unit configured to cause control data, which indicates an instruction for the external device, received from the control terminal via the proximity communication unit to be transmitted to the external device via the wireless communication unit, the control unit adjusting a transmission timing of the control data based on an operation state of equipment that emits the radio waves belonging to a predetermined frequency band or transmitting an instruction for changing the operation state of the equipment to the equipment,
   wherein the external device has the equipment individually having priority,
   wherein the control data includes identifier (ID) information allocated to each piece of equipment and instruction information for an instruction for an operation of the equipment,
   wherein a storage unit configured to store equipment information in which the ID information is associated with the priority is further included; and
   wherein the control unit identifies the priority of the equipment of an object to be controlled based on the ID information and the equipment information included in the control data, determines equipment of which an operation state is changed based on the identified priority and the priority of each piece of equipment indicated by the equipment information, and transmits an instruction for changing the operation state of the equipment to the equipment.

4. The wireless communication device according to claim 3, wherein the control unit adjusts the transmission timing of the control data to a timing at which generation of electromagnetic noise caused by the equipment is determined to be small.

5. The wireless communication device according to claim 3, wherein the wireless communication unit has a function of performing wireless communication of image data with the external device, and transmits the control data to the external device using the function.

6. A wireless communication system comprising:
a wireless communication device including:
a first wireless communication unit configured to perform wireless communication using radio waves belonging to a predetermined radio wave band between a first external device and a second external device;
a first proximity communication unit configured to perform proximity communication with a control terminal; and
a first control unit, which is a control unit configured to cause control data, which indicates an instruction for the first external device, received from the control terminal via the first proximity communication unit to be transmitted to the first external device via the first wireless communication unit, the first control unit adjusting a transmission timing of the control data or the data when causing the control data to be transmitted to the first external device while the first external device or the wireless communication unit sequentially transmits data to the second external device;
the control terminal including:
a generation unit configured to generate the control data; and
a second proximity communication unit configured to perform proximity communication with the wireless communication device; and
the first external device including:
a second wireless communication unit configured to perform wireless communication using the radio waves belonging to the predetermined radio wave band between the second external device and the wireless communication device; and
a second control unit configured to perform control based on the control data received from the wireless communication device via the second communication unit.

7. The wireless communication system according to claim 6,
wherein the control data includes ID information allocated to each piece of equipment of an object to be controlled and instruction information for an instruction for an operation of the equipment,
wherein the control terminal includes a reading unit configured to read the ID information from a display screen of an image display device having an information transmission function of optically transmitting the ID information using part of the display screen on which an image is displayed, and
wherein the generation unit generates the control data using the ID information read from the display screen.

8. A wireless communication system comprising:
a wireless communication device including:
a first wireless communication unit configured to perform wireless communication using radio waves belonging to a predetermined radio wave band with an external device;
a first proximity communication unit configured to perform proximity communication with a control terminal; and
a first control unit, which is a control unit configured to cause control data, which indicates an instruction for the external device, received from the control terminal via the first proximity communication unit to be transmitted to the external device via the first wireless communication unit, the first control unit adjusting a transmission timing of the control data based on an operation state of equipment to emit the radio waves belonging to a predetermined frequency band or transmitting an instruction to change the operation state of the equipment to the equipment;
the control terminal including:
a generation unit configured to generate the control data; and
a second proximity communication unit configured to perform proximity communication with the wireless communication device; and
the external device including:
a second wireless communication unit configured to perform wireless communication using the radio waves belonging to the predetermined radio wave band with the wireless communication device; and
a second control unit configured to perform control based on the control data received from the wireless communication device via the second communication unit.

9. The wireless communication system according to claim 8,
wherein the control data includes ID information allocated to each piece of equipment of an object to be controlled and instruction information for an instruction for an operation of the equipment,
wherein the control terminal includes a reading unit configured to read the ID information from a display screen of an image display device having an information transmission function of optically transmitting the ID information using part of the display screen on which an image is displayed, and
wherein the generation unit generates the control data using the ID information read from the display screen.

* * * * *